United States Patent
Dinamarca Tapia et al.

(10) Patent No.: US 9,629,882 B2
(45) Date of Patent: Apr. 25, 2017

(54) **STRAIN OF *COBETIA MARINA* AND BIOSURFACTANT EXTRACT OBTAINED FROM SAME**

(75) Inventors: Miguel Alejandro Dinamarca Tapia, Valparaiso (CL); Juan Ricardo Ojeda Herrera, Valparaiso (CL); Claudia Jimena Ibacache Quiroga, Valparaiso (CL)

(73) Assignee: UNIVERSIDAD DE VALPARAISO (CL)

( * ) Notice: Subject to any disclaimer, the term of this patent is extended or adjusted under 35 U.S.C. 154(b) by 561 days.

(21) Appl. No.: 14/122,529

(22) PCT Filed: May 30, 2012

(86) PCT No.: PCT/IB2012/052724
§ 371 (c)(1),
(2), (4) Date: Nov. 26, 2013

(87) PCT Pub. No.: WO2012/164508
PCT Pub. Date: Dec. 6, 2012

(65) Prior Publication Data
US 2014/0186475 A1 Jul. 3, 2014

(30) Foreign Application Priority Data
May 31, 2011 (CL) .................................. 1286-2011

(51) Int. Cl.
| | | |
|---|---|---|
| *C12N 1/12* | (2006.01) | |
| *C12N 1/20* | (2006.01) | |
| *C12P 1/00* | (2006.01) | |
| *C12P 1/04* | (2006.01) | |
| *A01N 63/02* | (2006.01) | |
| *A61K 35/74* | (2015.01) | |
| *A01N 63/00* | (2006.01) | |
| *C09D 5/16* | (2006.01) | |
| *C12R 1/01* | (2006.01) | |
| *A23K 50/80* | (2016.01) | |

(52) U.S. Cl.
CPC .............. *A61K 35/74* (2013.01); *A01N 63/00* (2013.01); *A01N 63/02* (2013.01); *A23K 50/80* (2016.05); *C09D 5/1625* (2013.01); *C09D 5/1687* (2013.01); *C12N 1/20* (2013.01); *C12P 1/04* (2013.01); *C12R 1/01* (2013.01)

(58) Field of Classification Search
None
See application file for complete search history.

(56) References Cited

U.S. PATENT DOCUMENTS

2008/0095871 A1* 4/2008 Riquelme Salamanca ............ A01N 63/02 424/780

FOREIGN PATENT DOCUMENTS

| JP | 2008194026 | 8/2008 |
|---|---|---|
| WO | WO 2007/043657 | 4/2007 |

OTHER PUBLICATIONS

Romanenko et al. International Journal of Systematic and Evolutionary Microbiology (2013), 63, 288-297.*
International Search Report for International Application No. PCT/IB2012/052724 mailed Oct. 23, 2012 (4 pages).
Maki et al. Substratrum/bacterial interactions and larval attachment: films and expolysacchardies of Halomonas marina (ACTCC 25374) and their effect on barnacle cypride larvae, *Balanus amphitrite* Darwin. *J. of Bioadhesion/Biofilm Research*. vol. 16(2-4). 2000. pp. 159-170.
Olivera et al. "Isolation and characterization of biosurfactant producing Alcanivorax strains: hydrocarbon accession strategies and alkane hydroxylase gene analysis." *Research in Microbiol*. vol. 160. 2009. pp. 19-26.
Satpute et al. "Biosurfactants, bioemulsifiers and expolyysaccharides from marine microorganisms." *BioTech. Adv*. vol. 28. 2010. pp. 436-450.

* cited by examiner

*Primary Examiner* — Chris R Tate
*Assistant Examiner* — Douglas F White
(74) *Attorney, Agent, or Firm* — Merchant & Gould P.C.

(57) ABSTRACT

The invention discloses a bacterial strain of non pathogenic *Cobetia marina* useful in aquaculture, corresponding to an isolated *Cobetia marina* strain, Gram negative, oxidase positive, deposited under registry number CECT N°7764; grows with dibenzothiophene (DBT) as the only carbon source. Also disclosed is a method to obtain a biosurfactant surfactant extract comprising growing strain *Cobetia marina* (MM1IDA2H-1) CECT N° 7764 in a reactor with liquid growth medium from 24 to 48 hours at a temperature between 10 and 35° C., pH 6 to 8; constant stirring between 100 to 400 rpm and oxygen saturation between 10 to 21%; until obtaining a grown cell culture and extracellular products plus inorganic salts; separating the cells, lyophilizing supernatant, sieve the obtained powder and dry. Further disclosed is a biosurfactant surfactant and uses thereof for treating infectious pathologies in aquaculture; use as additive for paint formulations for submergible surfaces; and use as food additive for fish, for inducing an immune response.

10 Claims, 6 Drawing Sheets

Fig. 4

Fig. 5A

STRAIN OF *COBETIA MARINA* AND BIOSURFACTANT EXTRACT OBTAINED FROM SAME

Figure 1:
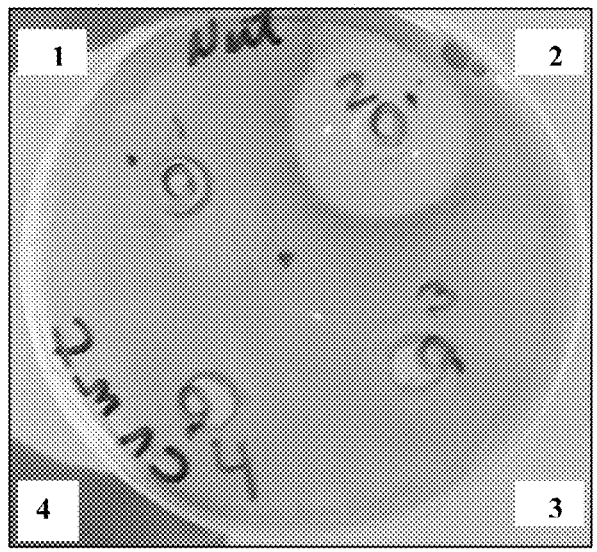

This application is a National Stage Application of PCT/IB2012/052724, filed 30 May 2012, which claims benefit of Serial No. 1286-2011, filed 31 May 2011 in Chile and which applications are incorporated herein by reference. To the extent appropriate, a claim of priority is made to each of the above disclosed applications.

The present invention is in the context of microorganism biotechnology, and is related to a new bacterium *Cobetia marina*; which is able to metabolize petroleum hydrocarbons and produce a biosurfactant with emulsifying and biological properties which allow, in a specific manner, to avoid infectious pathologies in fish and, unlike antibiotics, does not generate resistance. Furthermore, the invention discloses a biosurfactant extract and its use as an additive for food industry and for paint and coating industries.

OBJECT OF THE INVENTION

The object of the present invention is isolating and obtaining a new strain of *Cobetia marina* deposited under registry CECT N° 7764 in the Spanish Type Culture Collection (arbitrarily denominated MM1IDA2H-1 herein). The bacterial strain of this invention is relevant as it produces and releases to the supernatant medium a biosurfactant, separated or in a mixture, characterized by its capacity to interfere with the cellular communication system known as Quorum Sensing (QS) affecting the formation of microbial biofilms and/or viral behavior of pathogenic bacteria. Said supernatant can be extracted through a bioprocess for obtaining a concentrated extract thereof; which can be used for controlling microbial pathologies. The disclosed bioprocess of the present invention consists in growing *Cobetia marina* strain MM1IDA2H-1 in a bioreactor under preferred physical and chemical conditions, using dibenzothiophene (DBT) or petroleum industry waste rich in DBT as only carbon source for growing, and afterwards; separating, isolating and purifying a surfactant and bioactive extracellular extract, wherein its features are measured as its capacity to (i) act as emulsifier and (ii) interfere with the QS communication system of pathogen microorganisms, affecting formation of microbial biofilms and viral behavior of pathogenic bacteria, in particular, fish pathogenic bacteria.

The extract of extracellular medium wherein the *Cobetia marina* strain MM1IDA2H-1 was grown under favorable conditions of the present invention, corresponds to a biosurfactant (arbitrarily denominated herein as AAFOB-1IDA2H biosurfactant), characterized by presenting specific biological activity of high interest and applicability, for aquaculture industry as well as biomedicine; for controlling losses due to microbial pathological infections and/or to avoid formation of microbial biofilms. Also, AAFOB-1IDA2H biosurfactant presents emulsifying features that allow its incorporation into, for example, food and/or paint coatings.

Additionally, the present invention is also referred to the use of the strain of the present invention in form of a probiotic for food intake in preferred aquiculture species, with no harm caused in aquaculture species and benefiting their immunity.

STATE OF THE ART

Currently, the use of antibiotics in aquaculture is a control measure for infectious pathologies, but presenting complications and limitations threatening stability and consolidation of food products for human consumption generated in this activity. The most evident complication is based in that the use of antibiotics has not avoided economic and social losses derived from bacterial and pathogenic viral sprouts affecting production in aquaculture more particularly salmon culture, where great mortality is registered. At the same time, among the main limitations is the fact that antibiotics used in aquaculture do not substantially varies from the ones used in human health. Therefore, and just like with human health, currently the use of antibiotics in aquaculture is greatly restricted through norms and regulations that, for example, prohibit the use of these agents as weight gain strategies, or restrict their continual use during production process for controlling infectious pathologies.

Lack of efficacy of antibiotic treatments as well as restrictions to their use, are explained by the gradual increase in epidemic sprouts, in human as well as in animals, generated by pathogenic microorganisms that are resistant to the available variety of antibiotics. Antibiotics used in aquaculture are of bacteriolytic, bacteriostatic or bactericide type; all of which show the disadvantage that their application implies positive selection of resisting microorganisms, affecting therapies and, therefore, persistence of the infectious pathology.

On the other hand, antibiotic therapy practice in open spaces in aquaculture is not specific against pathogenic microorganisms, and can also affect beneficial microorganisms that are part of marine and/or fresh water microbial communities, altering stability and functioning of corresponding environments. Just as well, the use of antibiotics in open spaces can increase the number of genetic determinants associated with resistance to previously selected antibiotics, which eventually can reach species of microorganisms that are pathogenic for humans, representing a risk for human health. Currently, antimicrobial therapies used in aquaculture consider the administration of an active agent in food (medicated food). The doses are given as a function of body weight (kg) during periods of time (days). Some of the currently use therapies are summarized in the following table.

| Antibiotic | Dose * in food (mg/kg fish per day) | Time Days | Recommendation |
| --- | --- | --- | --- |
| Amoxicillin | 160 | 10 | Wide spectrum |
| Flumequine | 16 | 10 | Quinolone for septicemia |
| Florfenicol | 10 | 10 | Wide spectrum |
| Erythromycin | 100 | 21 | Macrolide against Gram + (BKD) |
| Oxytetracycline | 75 | 21 | Wide spectrum |
| Penicillin | 80 | 10 | Wide spectrum |

* Active agent

Treatment is administered to fish through food, by quantified mixing with the antibiotic. Once the mixture is made, the food is delivered to cultures through dispersion in water. In this procedure the food intake is not controlled and an important proportion of food is not consumed, with the consequent release of antibiotic to the environment. Since aquaculture is an activity directed to production of food for human consumption, current antibiotic treatments conditions innocuousness and safety of these products, and therefore affecting stability and consolidation of said products in their respective demanding markets.

In this context, current tendencies are looking for alternatives to using antibiotics, which considers solutions of natural origin that are specific, do not generate resistance, are not toxic or do not produce damages to the environment. One of the approaches for replacement of antibiotics comprise the search of new microorganisms considered probiotic and/or molecules of natural origin, such as biosurfactants.

Use of probiotic microorganisms for controlling infectious pathologies have been defined as a strategy of great interest in human health as well as in aquaculture. The concept of probiotic microorganism in aquaculture includes bacteria, cyanobacteria, microalgae, and fungi, among others. Just as well, the term probiotic can be broadened to include "normal microbiota", "effective microbiota" and/or "beneficial microorganism". Currently, the concept of probiotic in aquaculture is broadened to microorganisms that when used during productive processes improve the quality of water and/or inhibit pathogen generating diseases in species in culture. There are practices in aquaculture directed to removal of microorganisms present in water in a non-specific manner through the use of filters, ozone, and ultraviolet irradiation. These procedures alter aquatic microbial environments generating disequilibrium between beneficial microbiota and pathogenic microorganisms, favoring appearance of infectious pathologies, due to the loss of biological control among species. In this sense, search for new antagonist beneficial microorganisms controlling populations of pathogenic microorganisms through a competitive exclusion mechanism, is an alternative for the control of losses due to infectious pathologies.

Competitive exclusion mechanisms among microorganisms can be variate and are from producing molecules that kill (antibiotic) the competitors, to complex modulation systems considering the production of metabolites that alter the genetic program of competitors, altering for example, the virulence behavior of pathogenic microorganisms. These compounds do not have as exclusive function the competence, and in general can be produced by the microbial metabolism under varied circumstances.

On the other hand, the mentioned probiotic microorganisms, such as prebiotic bacteria, can produce natural molecules of microbial origin, surfactants, and/or emulsifiers, with hydrophobic and hydrophillic structures; and in this manner partitioning the interface between fluid phases with different polarity degrees, such as, air-water or oil-water interfaces. Said molecules or mixtures thereof are known as biosurfactants.

In spite that surfactants of major use are chemically synthetized, in the last decades the development and production of surfactants of biological origin has increased. This great interest is explained by the potential applications in environment protection, petroleum industry, human health and food industry. Applications are based mainly in its physical-chemical behavior, environment safety and low toxicity. Examples of use are from depuration of contaminated environments to formulation of products destined to health areas. For example, in the pharmaceutical industry, biosurfactants are used in cosmetics as non-toxic emulsifier agents.

Biosurfactants are classified according to their chemical composition and according to the microbial origin. General classification of biosurfactants according to their components groups them in: glycolipids, lipopeptides, phospholipids, fatty acids, and lastly polymeric or particulated surfactants. In the group of glycolipids, the most known correspond to rhamnolipids, described for the first time in a *Pseudomonas aeruginosa* bacteria, which are characterized by presenting one or two rhamnose molecules associated to one or two β-hydroxydecanoic acid. Among the lipopeptides, stands out surfactin produced by *B. subtilis* ATCC 213322). Other known biosurfactants correspond to liposan (*Candida lipolytica* and emulsan (*Acinetobacter calcoaceticus* strain RAG-1), both polymeric surfactants formed by polysaccharide-protein complexes.

Development of new biosurfactants and molecular level studies indicate that these compounds have important physiological and ecological functions for the microorganism producing them. For example, it has been determined the function of surfactants in bacterial motility, cell signaling processes and cellular differentiation. Production of biosurfactants by microorganisms is associated to competence mechanisms with other microorganisms. Some of them can be an alternative to the use of synthetic compounds or antimicrobial agents (antibiotics) due to their effectiveness, therapeutic specificity and low toxicity. According to performed research, biological activity shown by biosurfactants is not referred to their detergent properties, but to their specific molecular and physiological mechanisms. In this context, antimicrobial and immunomodulating properties are currently very attractive, where a wide variety of applications exist. For example, it has been established that surfactants have the capacity to modify microbial behavior when in relationship with cell communication, wherein certain genes related to compound synthesis of surfactant nature, respond to the presence of specific chemical signals.

More specifically, it is submitted that biosurfactants can interrupt the Quorum Sensing (QS) communication system; thus avoiding pathogenicity of microorganisms affecting other organisms of interest. In particular, it has been determined that formation of biofilms and microbial pathogen virulence depend, in many cases, of the molecular mechanism denominated Quorum Sensing (QS), characterized by corresponding to a microbial density dependent mechanism and by using specific chemical molecules as inter-cell signals. Said chemical signals are constantly produced inducing a coordinated group response when cell density is high. Molecules mediating the QS signal are denominated autoinducers, and are produced in basal levels in the microorganism. It has been identified a great variety of signaling molecules, where the most studied are from the homoserine lactone (AHLs) family.

Given that pathogenicity of microorganisms is related to the expression of virulence factors allowing access, colonize, disseminate and proliferate in the host causing associated damage. In many cases, the virulence factors are produced only under specific conditions, thus different pathogenic microorganisms have different mechanisms destined to coordinate expression of these factors with presence and eco-physiological features of the host organism. Under these conditions, some pathogenic bacteria also trigger the pathogenic behavior, forming biofilms, and can be resistant to the presence of antibiotics.

In this context and given that the communication system denominated Quorum Sensing (QS) is effectively present in pathogenic bacteria of fish, such as *Listonella anguillarum* and *Aeromonas salmonicida*; currently it is proposed that one of the treatment variables for infectious diseases in fish should be focused in inhibiting and/or stimulating the QS system of pathogenic bacteria.

Treatment of infectious diseases affecting fish are performed by procedures of: (i) vaccine immunization; (ii) antimicrobial therapy; and (iii) prophylaxis and hygiene management procedures during all the production process; all of which do not constitute specific procedures and generate damage to microbial ecosystems, further exhibiting a limited efficacy, quantifiable by economic losses due to fish mortality by infections; currently an increasing demand exists for the search of new products able to combat infectious pathologies with greater efficiency.

In this manner, the inhibition mechanism of cellular communication depending of Quorum Sensing is one of the alternatives of current treatments to avoid and treat infectious pathologies, since this is a selective control strategy, does not generate resistance and is environmentally compatible since no environmentally important microorganisms are eliminated.

Search and development of natural inhibitors for Quorum Sensing system is based on the competence existing between microorganisms and their ecosystems, wherein, in many cases, it has evolved from an interaction based on communication systems of QS. Therefore, interference of QS circuit, with consequent modification of genetic program of the opponent microorganism, is denominated Quorum Quenching (QC). Artificially, it is possible to generate QC by (i) using of molecules similar to AHLs imitating their structure binding to the corresponding receptor, avoiding the response of the circuit, or (ii) by degrading respective AHLs signals using lactonase and/or acylase enzymes which, respectively, break the lactone ring or hydrolyze the lateral chain of the same ring.

There are patents referred to the Quorum Sensing mechanism, some of them are directed to methods for inhibiting this system and thus avoiding the microbial pathologies. Among those documents is patent application WO/2002/00035 A1, which is directed to a food and its method of production with the end of using it in the aquaculture industry for controlling infectious pathologies in fish. Said application describes the use of bacteria of genera *Bacillus*, *Paenibacillus* and *Alteromonas* as probiotic microorganisms for controlling pathogens by competitive exclusion mechanism. Also, the patent describes incorporation of furanones in food as compounds destined to inhibit QS system. In both cases the use of synthetic surfactants is considered as a method to form emulsions with bacteria and/or active agents. This application does not mention bacteria of *Cobetia* genera and neither suggests the mechanism by which produced biosurfactants could generate an effect in signals involved in Quorum Sensing. Also, there are no patent documents describing the use of biosurfactants and/or surfactant molecules that are able to perform a molecular quenching of signals involved in Quorum Sensing.

On the other hand, other documents in prior art mention or describe the use of microorganisms similar to the strain of the present invention. Patent application JP2009034094, for example, describes a new microorganism of *Cobetia* genera, strain FERM P-21295, and mutant strains thereof. In this application a method is disclosed for production of polysaccharides, after isolation and culture of strain FERM P-21295. Said polysaccharides obtained from this strain, comprise structural components such as N-acetyl-D-glucosamine, D-galacturonic acid, N-acetyl-D-galactosamine, D-galactose, piruvic acid and D-alanin. In this document is disclosed the use of polysaccharides in cosmetics, medicines, and as a food additive; emphasizing the stability degree thereof and a notorious effect in suppressing melanin production.

Patent application JP2008194026A, describes a new *Cobetia* microorganism (FERM P-21101), that when cultured under convenient conditions produces a mucopolysaccharide acid. This application also teaches a method, consisting in cultivating a *Cobetia marina* microorganism, producing the mucopolysaccharide in the culture medium, obtaining the culture solution, and isolating the mucopolysaccharide acid with no selective elimination of the sulfated mucopolysaccharide from the culture solution.

The *Cobetia marina* microorganism is useful for producing the mucopolysaccharide useful as a dermatological medicine, cosmetics, useful for preventing pigmentation, liver point, freckles, chloasma, sunburn. It can also be used in prodrugs and pharmaceutical products.

Nevertheless, none of documents JP2009034094 or JP2008194026A teaches similar or close features to the extract of the present invention, furthermore, the utility products disclosed therein correspond to polysaccharides or mucopolysaccharides, and not fatty acids in an extract featuring surfactant activity, as the case of the present invention. Also, none of them makes reference to the use of *Cobetia marina* as a strain producing QS inhibiting compounds, unlike the present invention, wherein strain MM1IDA2H-1 of *Cobetia marina* is used as a producing source of surfactant molecules forming lipidic structures that can interact with QS signals inhibiting behavior of pathogenic microorganisms and/or stimulating immunity in cultured animals.

DESCRIPTION OF THE INVENTION

The present invention is based in the following figures, which are briefly described here below:

FIG. 1 corresponds to a bioassay in agar plate for detecting inhibitors for Quorum Sensing system with biosensor *Chromobacterium violaceum*. The picture shows the culture in a nutritive agar plate of a double layer of bacteria *C. violaceum* producing violacein pigment depending on the presence of signaling molecules of the QS system. The clear zone with no blue-violet color indicates an inhibition zone (+) for production of violacein, which is produced by induction of QS system by signals of the homoserine lactone type, given the activity of the filtered supernatant of strains of the invention in well 2. Well 4 corresponds to negative (−) control corresponding to culture medium with no bacterial growth.

Figure 2:
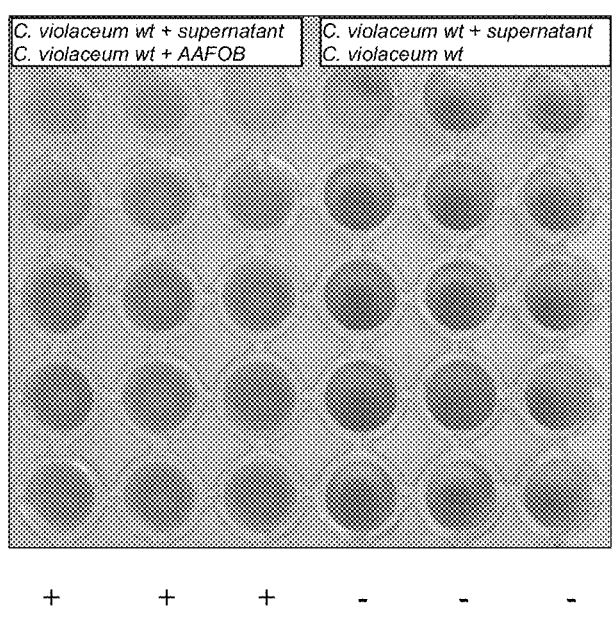

FIG. 2 corresponds to a microplate bioassat for detecting bacteria producing Quorum Sensing system inhibitors. The bioassay was performed with liquid cultures of biosensor *C. violaceum* grown in presence of filtered supernatant of a culture of strain MM1IDA2H-1 grown in Bushnell-Hass medium using DBT as the only carbon and energy source. As control (c), cultures of *C. violaceum* exposed to Brushnell-Hass culture medium that was not inoculated with strain MM1IDA2H-1 were used. The blue-violet color indicates the presence of violacein pigment (− sign), which is produced when certain chemical signals activate QS system. The presence of inhibitors of QS system is determined by the loss of blue-violet color (+ sign).

Figure 3:
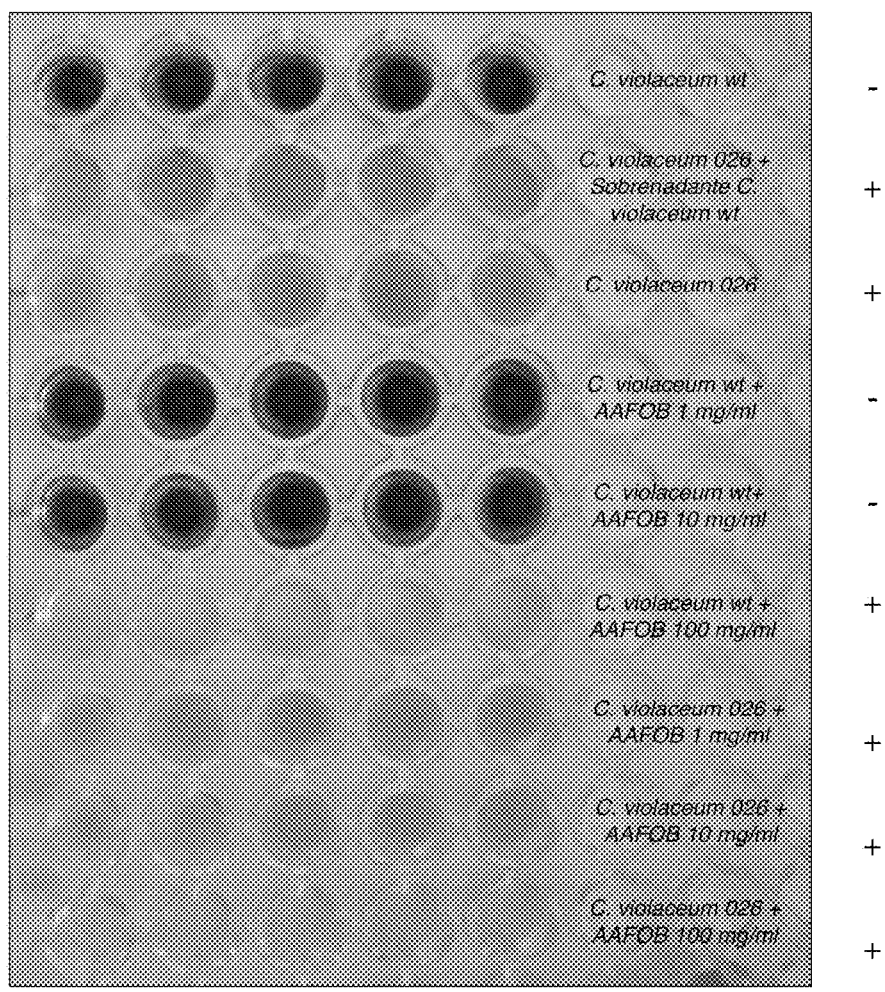

FIG. 3 corresponds to a microplate bioassay for evaluating the inhibiting effect on the Quorum Sensing communication system of the extracellular biosurfactant extract of strain MM1IDA2H-1. *C. violaceum* cultures were grown in the presence of extracellular surfactant extract (AAFOB) produced by strain MM1IDA2H-1 grown in Bushnell-Hass medium with DBT as the only carbon and energy source (wherein the inhibitory activity is simbolized by + sign).

Figures 4, 5A:
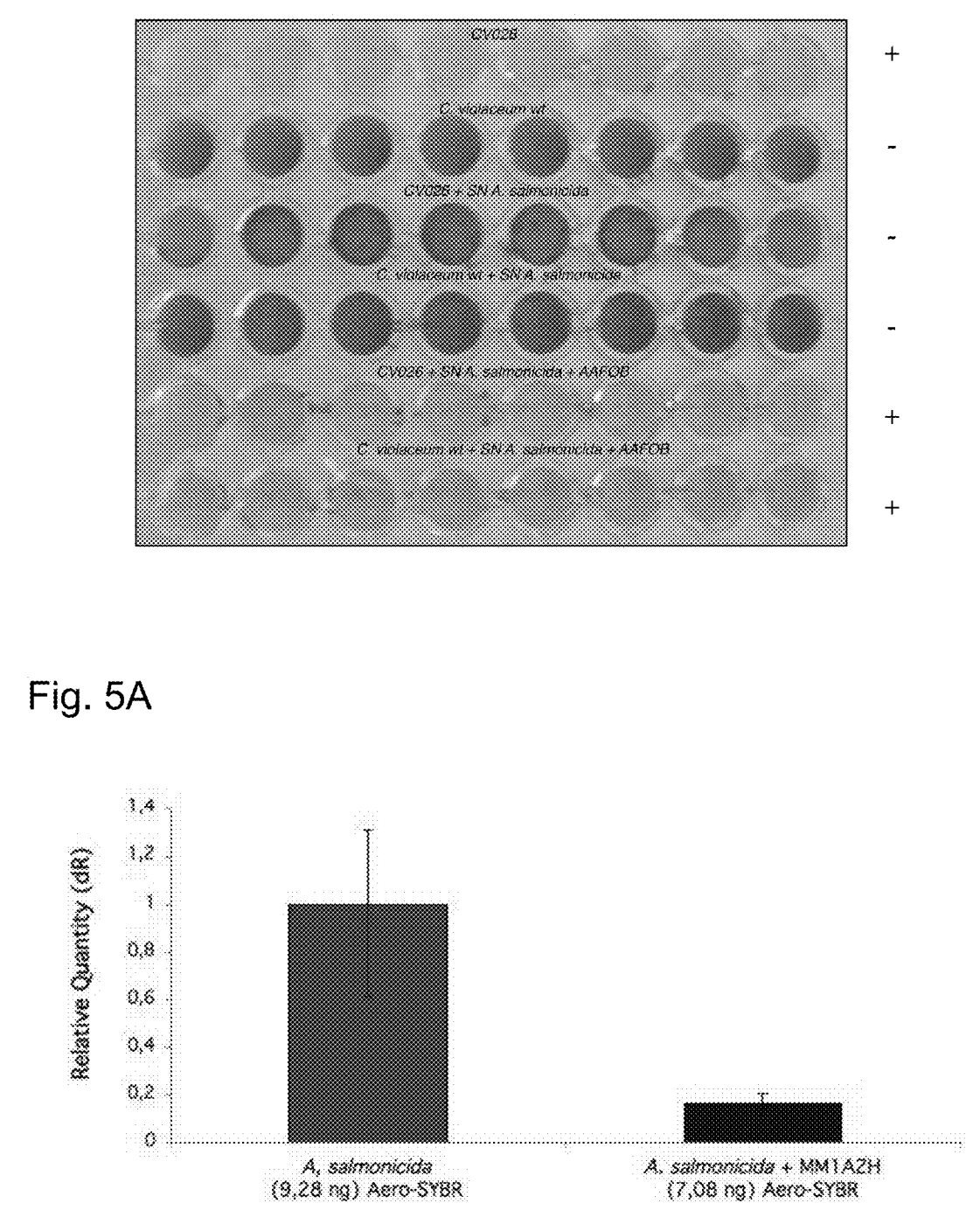

FIG. 4 corresponds to a microplate bioassay for evaluating the inhibitor effect of surfactant extract AAFOB for Quorum Sensing signals generated by fish pathogenic bacteria *Aeromonas salmonicida*. (wherein inhibitory activity is simbolized by + sign).

Figure 5B:
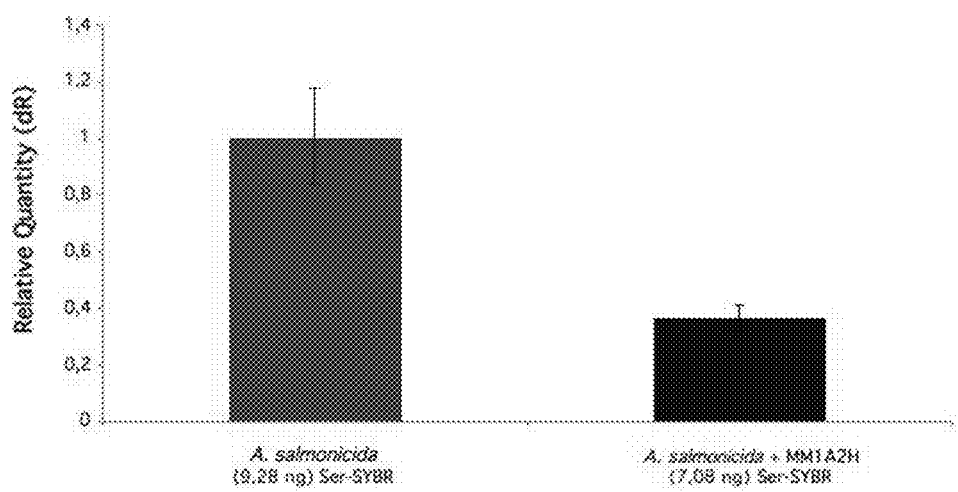
Figure 5C:
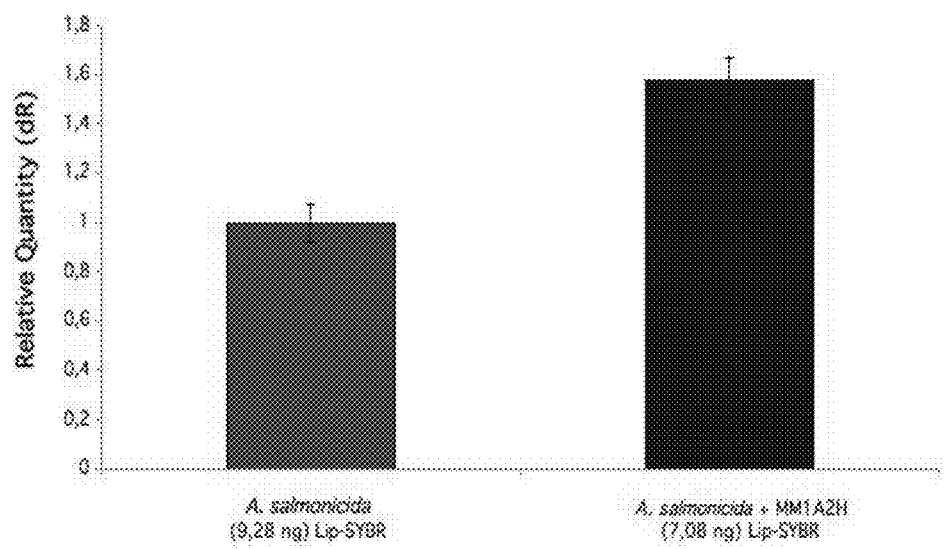

FIG. 5 shows graphically the antiviral activity of the extract against pathogenic bacteria *Aeromonas salmonicida*.

The activity was measured in relation to the virulence genes expression: aerolisine (A), serine protease (B) and lipase (C) of said pathogenic strain, in control conditions (no treatment) and when treated with the biosurfactant extract of the present invention.

Figure 6:
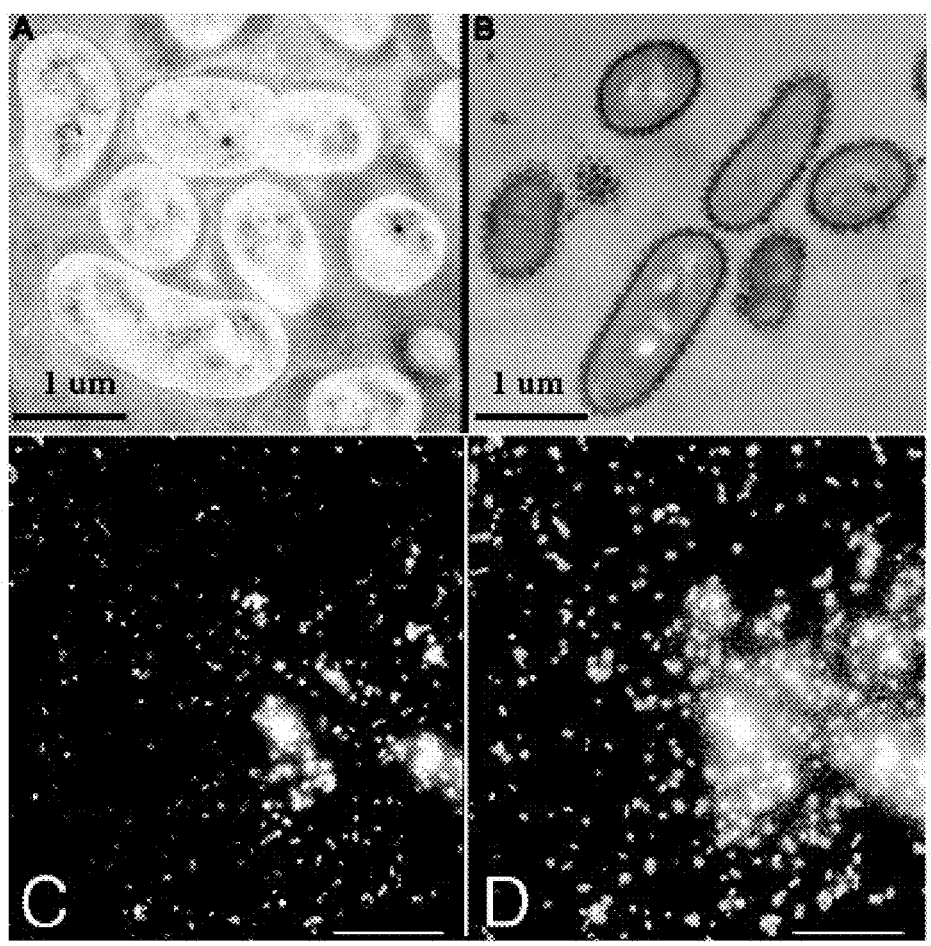

FIG. 6 shows an electron transmission microphotograph of bacteria cell of strain MM1IDA2H-1 that were grown in minimal Bushnell-Hass medium with succinate (30 mM) as the only energy and carbon source (A) or in minimal Bushnell-Hass medium with DBT (1% w/v) as the only energy and carbon source (B). (C) and (D) correspond to microphotographs of epifluorescence, equivalent to (A) and (B), using BODIPY dying for visualization of fatty acids.

Figure 7:
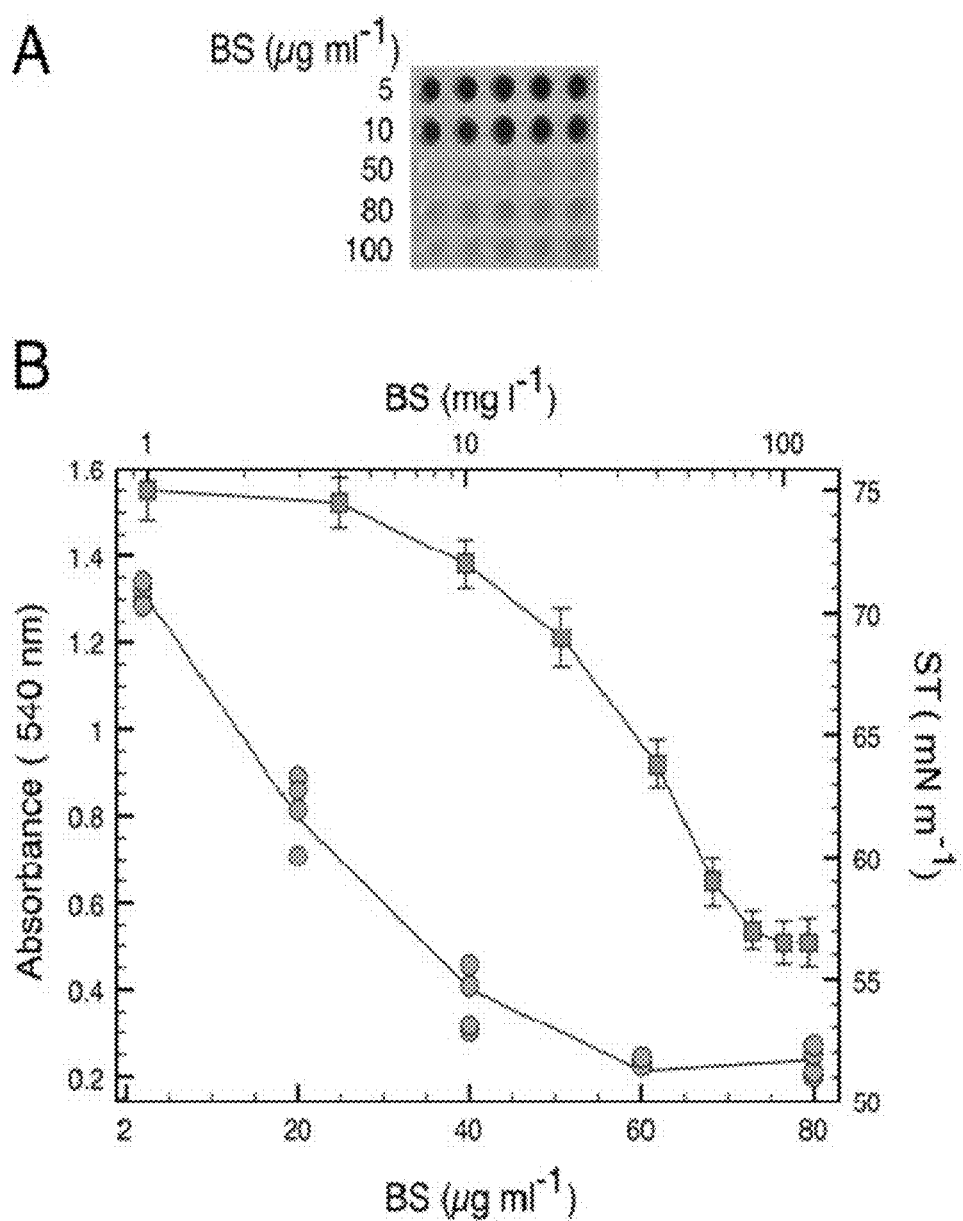

FIG. 7 shows a microplate bioassay of phenotype inhibition dependent of Quorum Sensing using Cobetia marina MM1IDA1H-1. (A) shows the purple phenotype response of C. violaceum to different concentrations (µg ml/L) of produced biosurfactant (BS). (B) shows surface tension of water (ST) at different concentrations (mg l/L log-scale) of biosurfactant (□), and its effect on biofilm formation of L. anguillarum (○). Critical micelle concentration was established at 80 mg l/L. Maximal values of phenotype inhibition depending on Quorum Sensing were corresponding to micelle formation concentrations.

In a first embodiment, the invention provides a new probiotic bacteria denominated Cobetia marina strain MM1IDA2H-1 to avoid or treat infectious pathologies in aquaculture.

The bacterial strain of the present invention was isolated and selected among autochthonous microorganisms of marine environment able to degrade or metabolize insoluble organic compounds that are part of petroleum, that can be harmful to the environment. The substrate compounds useful for degradation are of aromatic and/or aliphatic type, which are solubilized in the aquatic medium so they can be assimilated by the microorganism. Said substrates are used by the microorganism for producing energy, cellular material and secondary metabolites. Cobetia marina bacteria strain MM1IDA2H-1, of this invention corresponds to an autochthonous strain of marine environment, that can grow in a wide range of saline concentration (sodium chloride), a wide range of temperature from 10° to 35° C. and uses aromatic or aliphatic organic compounds that are organic components of petroleum, as a source of energy and carbon, and therefore survives in marine environment. In a preferred embodiment, Cobetia marina strain MM1IDA2H-1 was grown with dibenzothiophene (DBT) as the only carbon and energy source, wherein the range for using said carbon source varies from 0.75 to 1.5% w/v; and wherein preferentially the DBT concentration used is 1% w/v in the culture and selection media.

The strain of the present invention was identified among bacteria of the genera Cobetia by comparison and determination of identity of the genome of the sequencing of the region corresponding to 16S ribosomal DNA, in particular to the polynucleotide of region 16S ribosomal RNA of the sequence of Cobetia spp microorganism. In this manner a new microorganism was isolated, which was deposited in the Spanish Type Culture Collection (Colección Española de Cultivos Tipo, CECT, University of Valencia, Parc Cienfific Universitat de València, Catedrático Agustin Escardino, 9 46980 Paterna (Valencia), SPAIN) with registry number 7764, and date of deposit of Jul. 5, 2010 (Cobetia marina strain MM1IDA2H-1). Given two very similar or identical sequences, discrimination was performed by using evaluation of physiological/biochemical parameters, such as: capacity for using different hydrocarbons, sensibility to antibiotics and enzymatic activities. As a comparison pattern, a reference bacteria denominated Cobetia marina CECT 4278 was used in characterization assays.

Unlike the reference species Cobetia marina CECT 4278, the Cobetia marina strain MM1A2DAIH-1 of the present invention is able to grow in DBT-like hydrocarbons, generating an extract that can decrease surface tension, act as emulsifier and generate an extract with a QS inhibitory capacity when grown in a culture medium with DBT as the only nutritive source, that is, as an energy and carbon source. The assays performed with the reference strain Cobetia marina CECT 4278 using methods of the technique, no capacity for using DBT and producing surfactants was determined. At the same time, from biochemical assays for determining existence of enzymes and/or characterizing metabolisms, it was established that differentiating features exist between reference strain of Cobetia marina and Cobetia marina strain MM1IDA2H-1 of this invention. In particular, it was possible to differentiate, in a simple and effective manner both bacteria, since Cobetia marina strain MM1IDA2H-1 has a positive reaction to oxidase reaction, while Cobetia marina CECT 4278 gives negative results for this test. On the other hand, it is of special interest the fact that Cobetia marina strain MM1IDA2H-1 does not present pathogenic features, i.e., it is safe, since Cobetia marina strain MM1IDA2H-1 does not show hemolytic activity when grown in a blood-containing culture medium.

In this sense, Cobetia marina strain MM1IDA2H-1 of this invention presents among its novel features: using petroleum-derived compounds, such as sulfured cyclic aromatic hydrocarbons; and generating biosurfactants with specific physical and biological activities. Therefore, it is possible to determine that Cobetia marina strain MM1IDA2H-1 is part of the group of beneficial microorganisms or also denominate probiotic for aquaculture.

In a second embodiment, the invention provides a method for producing biosurfactant AAFOB-1IDA2H using Cobetia marina strain MM1IDA2H-1 of the present invention, comprising the steps of:

(a) growing Cobetia marina strain MM1IDA2H-1 in a culture medium containing from 0.75 to 1.5% w/v of DBT or other sulfured cyclic aromatic hydrocarbons the only available carbon substrate for the bacterium, the medium further comprising at least: 0.2 g/L magnesium sulfate; 0.02 g/L calcium chloride; 1 g/L monopotassium phosphate; 1 g/L diammonium hydrogen phosphate; 1 g/L potassium nitrate and 0.05 g/L ferric chloride, all of them dissolved in distilled water;

wherein, alternatively, the strain of the invention can be grown in conditions similar to the ones already described, replacing 75% of the distilled water volume with a 75% of sea water as solubilizing agent;

stir between 100 to 400 rpm, during 24 to 48 hours under conditions of pH between 6 and 8, temperature between 10° and 35° C., oxygen saturation between 10-21%;

(b) separating the cells of the grown strain by centrifugation and further filtration;

wherein the centrifugation step is performed between 4,000 to 8,000 rpm for 15 to 20 minutes; and after discarding the sedimented phase, the supernatant is recovered, which is filtered using a filter with a cut-off between 0.22 and 0045 µm;

(c) lyophilizing filtered supernatant at −80° C. y 10 militorr (1.33 Pa);

(d) mechanically sieving the powder obtained in step (c), with horizontal stirring, for discarding impurities and salts; and (e) dry the sieved powder obtained in step (d) at a temperature between 30 and 50° C. for 20 to 30 horas, obtaining a dry light yellow powder constituted by fatty acids having emulsifying and bioactive properties. The more preferred conditions are, drying the powder at 40° C. for 24 hours.

The preferred embodiment of the present invention involves a method wherein the growth of the strain is performed in a commercial Bushnell-Hass (Difco) medium (medium comprising the salts mentioned in step (a)) or a medium formed in a 25% of said medium and 75% in volume of sea water; wherein the preferred concentration value of the only carbon source (DBT) is 1% w/v.

In a third embodiment, the invention provides a concentrated biosurfactant extract and surfactant with emulsifying and bioactive properties. Said biosurfactant extract is characterized by its chemical composition, its capacity for emulsifying and its biological activity.

The bioactive properties of biosurfactant extract of the invention (AAFOB-1IDA2H) are determined regarding its activity in forming biofilms and bacterial pathogenicity, activities that depend on the QS system.

The biological activity of the biosurfactant extract was determined on fish pathogenic bacteria such as *Listonella anguillarum* that forms biofilms favoring its dissemination. In particular, exposition of *Listonella anguillarum* to *Cobetia marina* strain MM1IDA2H-1 and/or biosurfactant extract of this invention, results in inhibition of biofilm formation of the indicated pathogen.

Also, *Cobetia marina* strain MM1IDA2H-1 can be used as a beneficial bacteria for avoiding pathologies caused by *Listonella anguillarum*.

Furthermore, the effect of the biosurfactant extract of the present invention on bacteria of *Aeromonas* that produce and release lytic extracellular proteins that are virulence factors controlled by QS, such as lipases and proteases, was determined, especially virulence dependent of QS mechanism of pathogenic bacteria and fungi can be inhibited, preferentially inhibition of virulence of pathogenic bacteria *Aeromonas salmonicida*.

Moreover, surfactant properties of biosurfactant extract of this invention are measured according to a decrease of surface tension or by its activity as emulsifier. Said surfactant properties allow incorporating these products as cosmetic, food additives and/or any other food or pharmaceutical formula.

*Cobetia marina* strain MM1IDA2H-1 is used in the present invention for producing a biosurfactant extract that has physical properties by acting as an emulsifier agent, with a surface tension value between 66 to 70 dynes/cm, and a high emulsion stability.

Extract AAFOB-1IDA2H of the present invention corresponds to a mixture of organic molecules composed of at least palmitic, myristic, linoleic fatty acids, specifically constituted by 2.52 to 9.22% lauric acid C12:0; 5.97 to 10.13% myristic acid C14:0; 2.4 to 2.88% pentadecanoic acid; 19.27 to 24.39% palmitic acid C16:0; 7.81 to 9.83 palmitoleic acid C16:1; 8.37 to 10.43% stearic acid C18:0; and 11.32 to 16.25% oleic acid C18:1 cis. This extract is obtained by biosynthesis performed by *Cobetia marina* strain MM1IDA2H-1 grown in a medium supplemented with DBT as the only carbon source.

Surfactant properties of microbial origin products, measured by its capacity of decreasing surface tension or acting as emulsifiers, are of great technological importance in cosmetic, food, and/or pharmaceutical formulations. In particular, emulsifiers provided by the biosurfactant extract of the present invention provide stability to formulations in which an active agent is incorporated, that requires dosing or delivering for using in cosmetics, pharmaceuticals, and food products among others. *Cobetia marina* strain MM1IDA2H-1 produces a surfactant supernatant that can reduce surface tension, being able to maintain stable emulsions of water-organic oil solutions, used in food industry as well as hydrocarbon solutions used in painting and/or coating industries.

On the other hand, the biological activity of the biosurfactant was evaluated in cultured fish for determining its toxicity and potential effect on fish immunity. In this sense, the extract product AAFOB-1IDA2H was not toxic (survival of 78%) for fish, and according to the immunity analysis with different markers, it was observed that it was able to stimulate the activity of the immunological agent TNF-alpha in trout gills.

Use of the biosurfactant extract AAFOB-1IDA2H extracellularly produced by the new bacterial strain, with physical emulsifier properties, and biological properties associated to selective inhibition of virulence mechanisms of pathogenic microorganisms for fish, implies a line of development of antimicrobial products for aquaculture of great value by being selective, non-toxic, not generating resistance and being environmentally safe. Thus, an additional embodiment of the present invention is referred to the use of the bioactive extract with emulsifier surfactant properties as a food additive and/or paint coatings. In particular, the biosurfactant can be used as a food additive in a food formulation granting functionality to the food; or this food additive is used for avoiding and treating infectious pathologies depending on QS system. An alternative embodiment uses extract AAFOB-1IDA2H in the formulation of bioactive coatings and/or paintings for submerged surfaces, being of special interest its use for control of microbial biofilms.

APPLICATION EXAMPLES

Bacterial Strains and Growing Conditions

Bacterial strains isolated from sea water samples were enriched in liquid Bushnell-Hass medium (Difco, Detroit USA) containing DBT (Merck, Hohenbrunn, Germany) as the only energy and carbon source. Growth temperature was 20° C. Bioassays for determining presence of inhibiting or stimulating QS system were performed using strains *Chromobacterium violaceum* (CECT 494 T; ATCC 12472) and *Chromobacterium violaceum* CV026 (CECT 5999; NCTC 13278; VTT E-82808)(Chu et al., 2011) which were grown at 26° C. in Luria Bertani medium. For strain *C. vilaceum* CV026 Kanamycin antibiotic (25 µg/ml) was added.

Isolation of *Cobetia marina* Strain MM1IDA2H-1.

*Cobetia marina* strain MM1IDA2H-1 of the present invention was isolated from sea water samples collected from intertidal coastal ponds in Renana zone, Viña del Mar, Valparaiso region, Chile. Water samples were used for performing a selective enrichment inoculating flasks with culture media and DBT as the only carbon and energy source. Flasks were incubated at 20° C. for 2 weeks. Cultures presenting growth were selected for performing isolation in a solid culture medium Difco™ Sea Agar ZoBell 2216 (Becton Dickinson and Co. USA). Plates were incubated at 20° C. and from them isolated colonies were selected for further analyses.

Microbiological Characterization.

Identification and characterization of *Cobetia marina* strain MM1IDA2H-1 was performed by the following studies: 1) molecular (amplification, sequencing, sequence analysis of rDNA 16S); 2) physiological (growth with different concentrations of sodium chloride); and 3) biochemical and metabolic assays (with Api 20 NE systems from Biomerieux and Ecoplate from BIOLOG). Sequencing and analysis of rDNA 16S region was performed in Spanish Type Culture Collection (Colección Española de Cultivos Tipo, CECT). For all comparative studies, reference strain of *Cobetia marina* (CECT 4278; ATCC 25374) was used.

Given the necessity to properly classify the new microorganisms present in Halomonadaceae family, taxonomical location of *Cobetia marina* MM1IDA2H-1 used in the present invention is based in molecular biology methods and in methods that would allow determination of features specific for said microorganisms, such as metabolism and NaCl salt requirements. All these techniques are reproducible and are part of the state of the art.

TABLE 1

Differences between *Cobetia* strain MM1IDA2H-1, *Cobetia marina* and *Halomonas halodurans*.

|  | *Cobetia marina* | *Halomonas halodurans* | MM1IDA2H-1 |
|---|---|---|---|
| Growth in: |  |  |  |
| Lactulose | − | − | + |
| Xylitol | − | − | + |
| Formic acid | − | − | − |
| D-Glucosaminic acid | − | + | + |
| Dibenzothiophene | ND* | ND* | + |
| Anthracene | ND* | ND* | + |
| Phenanthrene | ND* | ND* | + |
| Naphthalene | ND* | ND* | + |
| Hexadecane | ND* | ND* | − |
| Range of growth in NaCl (%) | 0.5-20 | 3-20 | 1-18 |
| Reaction of: |  |  |  |
| Oxidase | − | + | + |
| Nitrate reduction | − | − | − |
| ONPG | + | − | + |
| Lisine decarboxilase | + | + | − |
| Sensibility to: |  |  |  |
| Nitrofurantoin | + | − | − |
| Rifampicin | − | + | − |
| Trimethoprim-sulfamethoxazole | + | + | − |
| 16S rADN similarity to *Cobetia marina* | 100 | 100 | 100 |
| 16S rADN similarity to *Halomonas halodurans* | 100 | 100 | 100 |
| Production of biosurfactant surfactant extract (BS) using DBT. | ND* | ND* | + |
| BS extract production with properties against *A. salmonicida* | − | ND* | + |
| BS extract production for inhibiting QS system from *C. violaceum*. | − | ND* | + |

ND* Not described in literature

Evaluation of biosurfactant extract produced by *Cobetia marina* strain MM1IDA2H-1 was performed by evaluating surfactant properties. In particular, 12 colonies isolated in pure cultures were evaluated, grown independently in Bushnell-Hass culture medium (Difco, Detroit USA) with DBT as carbon source at 20° C. for 72 hours. The obtained cultures were centrifuged at 4,000 rpm for 20 minutes at 4° C. Supernatants of 12 strains obtained were filtered with cellulose filters of 0.22 μm and stored at 10° C. for surfactant properties analyses. The analysis for surfactant properties was performed using a DuNöy tensiometer, for which the supernatant of isolated microorganisms was used.

TABLE 2

Surface tension values.

| Strain | Surface tension (dynes/cm) |
|---|---|
| MM1A2AA | 77.2 |
| MM1A2AB | 77.3 |
| MM1A2C | 75.5 |
| MM1A2DA | 77.0 |
| MM1A2DB | 77.4 |
| MM1A2GB | 77.0 |
| MM1A2H | 68.0 |
| MM1A5A | 76.8 |
| MM1A5B | 77.0 |
| MM1A5C | 75.0 |
| MM1A5D | 77.0 |
| MM1A5E | 77.0 |

Table 2 shows 12 bacterial strains of marine origin that were isolated from sea water samples through a selective enrichment procedure using a minimal culture medium containing a petroleum-derived hydrocarbon as the only energy and carbon source. The compound for growth of the strain was dibenzothiophene, insoluble in aqueous phase. Once isolated, microorganisms were evaluated to determine its capacity to produce surfactant compounds, for this end, they were grown in liquid Bushnell-Hass medium from where 20 mL samples were filtered and centrifuged at 8,000 g. Final supernatant were used for measuring surface tension with a Dunoy tensiometer equipment. Values represent drop in water surface tension (TS).

Evaluation of Bioactive Properties.

Once determined surfactant property of supernatant, a bioassay was performed, destined to establish its capacity to inhibit or stimulate cellular communication mechanism known as Quorum Sensing (QS). The bioassay for determining existence of inhibitors of QS system used strain *Chromobacterium violaceum* and consisted in exposing this microorganism to the presence of a surpernatant of *Cobetia marina* strain MM1IDA2H-1. *Chromobacterium violaceum* has a QS circuit that when active induces the expression of genes coding for synthesis of violacein, a compound granting a violaceous phenotype to this bacterium. On the other hand, as an assay for determining the existence of a stimulation of QS system, *Chromobacterium violaceum* CV026 was used. This microorganism is derived from wild-type strain of *Chromobacterium violaceum* and unlike it, it has been mutated in its capacity to produce auto-inducing molecules with the insertion of a mini-trasposon with resistance to kanamycin antibiotic (miniTn5::Km). In this manner, this microorganism requires external chemical signals to activate QS circuit and generate the violet phenotype. For interference bioassays with QS system, supernatant from DBT degrading selected bacteria was used.

As a result of growing *Cobetia marina* strain MM1IDA2H-1 in a Bushnell-Hass medium (Difco, Detroit USA) containing DBT (Merck, Hohenbrunn, Germany) a supernatant is produced reducing surface tension of ultrapure water (high purity water, free of dissolved and suspended solids) at 68 dynes/cm (Table 2). This decrease is comparatively lower than the one obtained by strains that were isolated by their feature of growing in presence of DBT as carbon source. During their growth in these conditions, it is possible to appreciate by using transmission electron microscopy, the formation of lipidic structures that are secreted outside the cell (FIG. 6).

Supernatant produced by *Cobetia marina* strain MM1IDA2H-1 in a Bushnell-Hass culture medium (Difco, Detroit USA) containing DBT inhibits violet QS-dependent phenotype in *Chromobacterium violaceum* (check 2 in FIG. 1 and FIG. 7). On the other hand, no inducer effect was observed for QS system for *Chromobacterium violaceum* CV026. The non-inoculated medium did not produce inducer or inhibiting effect in corresponding bioassays (check 1 in FIGS. 1 and 7).

*Cobetia marina* strain MM1IDA2H-1 has a short-bacillus shape, Gram negative, oxidase positive, grows in a wide range of sodium chloride (Table 1). Does not present hemolytic activity and thus is not considered a pathogenic bacterium. In comparison to the description for the reference strain in prior art, *Cobetia marina* strain MM1IDA2H-1 metabolizes as a carbon source anthracene, naphtalene, and phenanthrene.

During growth in a Bushnell-Hass culture medium (Difco, Detroit USA) containing DBT as a carbon source, *Cobetia marina* strain MM1IDA2H-1 produces a supernatant with biosurfactant features that is bioactive by being able to inhibit the intercellular QS communication mechanism of *Chromobacterium violaceum*. There are no reports of bacteria from this genera that can use DBT as carbon source and synthesize biosurfactants having a biological activity. Degradation of this type of compounds as well as production of bioactive surfactant are considered positive features in marine origin bacteria and thus, explain their benefits for using in aquaculture.

*Cobetia marina* strain MM1IDA2H-1 produces extract AAFOB-1IDA2H with emulsifier properties of interest for food formulation, and formulation of bioactive coatings and/or paintings for submerged surfaces.

Obtaining AAFOB-1IDA2H Extract.

To obtain a surfactant extract from the supernatant produced by *Cobetia marina* strain MM1IDA2H-1, the bacteria was inoculated in 1 liter of Bushnell-Hass medium (Difco, Detroit USA) containing DBT as carbon source. Growth was performed in a bioreactor Fermentor Liflus model GX with automatic pH, oxygen, temperature and stirring controls. Incubation conditions were as follows: temperature of 30° C., aireation 100° A and stirring with rotating blades at 200 rpm for 48 hours. The obtained culture was centrifuged at 5,000 rpm for 20 minutes in an Eppendorf centrifuge, model 5810R and the supernatant was filtered with sterile 0.22 μm filters. Supernatant free of cells was treated with cold acetone (JT Backer, USA) in a 2:1 ratio for precipitation. The mixture supernatant/acetone was stored at −10° C. for 24 hours. The obtained precipitate was separated from acetone/water solution by centrifugation at 10,000 rpm at 4° C. in an Eppendorf centrifuge model 5810R. The obtained precipitate was dried at room temperature for 48 hours.

Emulsifier Index and Emulsion Stability Assays.

The emulsifier index of the extract with different organic phases was determined. The obtained extract was dissolved in ultra pure water at a concentration of 100 mg/mL. Emulsification assays were performed with hexadecane (Merck, Germany), commercial gasoil, commercial fish oil and commercial canola oil. The organic:aqueous phase ratios used were 1:1. Emulsions were formed by agitation in vortex for 2 minutes leaving tubes still for 24 hours. Once time passed, the emulsification index was measured at 24 hours ($E_{24}$) for which, the height of emulsion in centimeters was measured with respect to the total height of phases, expressing the result as a percentage. The stability of emulsion was determined by constant measurement of decay constant ($K_d$). For this, emulsions as previously described with different organic phases were prepared, measuring turbidity of aqueous phase at a wavelength of 540 nm. Ratios for organic and aqueous phases were 4:25, respectively. Measurements were performed at times: 10, 20, 30 40, 50 y 60 minutes after forming the emulsion. Decay constant ($K_d$) was calculated from the slope of data obtained in turbidity against time readings.

AAFOB-1IDA2H extract produced by *Cobetia marina* strain MM1IDA2H-1 during its growth in DBT as carbon source, has the property of acting as emulsifier and can maintain stable fish oil and canola oil emulsions (Tables 3 and 4).

TABLE 3

Emulsifier activity of AAFOB extract with fish and canola oils.

| AAFOB extract (mg/mL) | $IE_{24}$ (%) Fish oil |
|---|---|
| 200 | 71.4 |
| 400 | 69.6 |
| Control | 0 |

Compounds denominated surfactant can act as emulsifiers, which represents varied advantages in many productive processes in pharmaceutical and food industries. In this case, it is shown that the extract denominated AAFOB produced by strain MM1IAD2H when grown in dibenzothiophene can be used as emulsifier agent for oils such as canola or fish oils. The emulsification index (IE) measured as percentage indicates stability of emulsion formed by oil and water in presence of emulsifier agent, in a time determined in this case for 24 hours at 20° C.

TABLE 4

Emulsion stability of fish oil-water emulsion in presence of AAFOB measured as Decay Constant ($K_d$).

| | $K_d$ | |
|---|---|---|
| | Without AAFOB | With AAFOB |
| Fish oil | −0.007 | −0.001 +/− ×10$^{-3}$ |

Chemical composition of biosurfactant extract of this invention was determined, finding that the gas-mass chromatography profile (GC-M) shows a high contribution of 12 to 18 carbon atoms fatty acids (Table 5).

TABLE 5

Percentge of fatty acids present in the extract produced by *Cobetia marina* strain MM1IA2H-1.

| Fatty acid profile | Sample AAFOB-A | Sample AAFOB | Sample AAFOB-MM |
|---|---|---|---|
| % Lauric acid C12:0 | 9.22 | 2.52 | 3.87 |
| % Myristic acid C14:0 | 10.13 | 5.97 | 6.83 |
| % Pentadecanoic acid C15:0 | 2.88 | 2.54 | 2.40 |
| % Palmitic acid C16:0 | 24.39 | 20.98 | 19.27 |
| % Palmitoleic acid C16:1 | 9.83 | 8.46 | 7.81 |
| % Stearic acid C18:0 | 10.43 | 9.65 | 8.37 |
| % Oleic acid C18:1 cis | 13.29 | 16.25 | 11.32 |

Activity of biosurfactant extract AAFOB-1IDA2H produced by *Cobetia marina* strain MM1IDA2H-1 on virulence of *Aeromonas salmonicida* and biofilm formation of *Listonella anguillarum*.

For analyses of biofilm formation, *Listonella anguillarum* (CECT 522; ATCC 19264) was used grown at 20° C. in marine agar Difco™ from ZoBell 2216 (Becton Dickinson and Co. USA). *Listonella anguillarum* strain was grown at 20° C. in liquid marine medium containing: 10 g yeast extract; 10 g peptone; 750 ml filtered sea water; 250 ml distilled water. Virulence inhibition assays were performed using *Aeromonas salmonicida* strain (CECT 894 T; ATCC 33658) grown at 24° C. in nutritive broth or solid TSA medium. *A. salmonicida* as well as *Listonella anguillarum* were manipulated in a biosafety cabin ESCO Streamline model SC2 Class II BS. Bioassays were performed using *Chromobacterium violaceum* (CECT 494 T; ATCC 12472) and *Chromobacterium violaceum* CV026 (CECT 5999; NCTC 13278; VTT E-82808) strains that were grown at 26° C. in Luria Bertani medium. For *C. vilaceum* CV026 strain kanamycin (25 µg/ml) was added. Both strains were acquired from Spanish Type Culture Collection (Colección Española de Cultivos Tipo, CECT). *Cobetia marina* strain MM1IDA2H-1, was grown at 30° C. in Bushnell-Hass medium (Difco, Detroit USA) containing DBT as carbon source for 48 hours with 200 rpm stirring.

QS System Inhibition Bioassay with AAFOB-1IDA2H Extract.

With the obtained extract a bioassay directed to establish the capacity for inhibiting or stimulating the cellular communication mechanism known as Quorum Sensing (QS) was made. The bioassay for determining existence of inhibitors and/or stimulants of QS system was performed with *Chromobacterium violaceum* and *Chromobacterium violaceum* CV026 strains as previously described. *Chromobacterium violaceum* was grown in liquid Luria Bertani medium in 96-well microtiter plates at 30° C. For determining if the obtained extract interferes with the presence of QS signals, once reaching an optical density of 0.3 (at 600 nm), 50 µl of supernatant from liquid cultures of the same *Chromobacterium violaceum* and extract obtained from *Cobetia marina* strain MM1IDA2H-1 were added to each well (FIG. 2). The extract was used in concentrations of 300 mg/ml dissolved in LB culture medium For determining if the extract produced by *Cobetia marina* strain MM1IDA2H-1 produces effects on QS system during growth, *Chromobacterium violaceum* and *Chromobacterium violaceum* CV026 were grown in the presence of the extract of the present invention (FIG. 3).

Biofilm Inhibition Assay for *Listonella anguillarum* with AAFOB-1IDA2H Extract.

Biofilm formation or inhibition assay was developed with *Listonella anguillarum* CECT 522 acquired at the Spanish Type Culture Collection (Colección Española de Cultivos Tipo). This bacterium can form biofilms which is Quorum Sensing (QS) dependent behavior. The protocol used for evaluating adherence of *Listonella anguillarum* to 96-well microtiter plates was crystal violet dying. This method allows dying cells which have been adhered to a surface forming a biofilm. Quantitation was made by diluting dyed wells with ethanol-acetone and reading optical densities at an absorbance of 575 nm.

Inhibition of Virulence Factors in *Aeromonas Salmonicida* Assay.

For determining the effect of *Cobetia marina* of this invention on the QS dependent virulence factors of *Aeromonas salmonicida* an assay for quantitating the virulence gene expression when exposed to the biosurfactant extract was made. Evaluated genes were: 1) aerolisin, 2) serine protease, and 3) lipase. Said genes depend on QS mechanism in *Aeromonas salmonicida*.

The assay was performed growing *Aeromonas salmonicida* in a liquid broth medium (Oxoid, UK) in presence or absence of stimulus. For favorable effects and conditions of the study, the stimulus correspond to the result of exposure to compounds produced by *Cobetia marina*. *Aeromonas salmonicida* cultures were grown in Erlenmeyer flasks in an orbital shaker Companion model SK-300 at 20° C. and 200 rpm until reaching optical density of 0.8 ($Abs_{600nm}$). At this moment, cultures were centrifuged at 8,000 rpm at 4° C. and RNA extraction and purification was performed using RNeasy® Mini Kit (Quiagene Ambion Inc. Texas, USA). cDNA formation reaction and amplification were performed with one step system Brillant III Ultra Fast SYBR® Green QRT-PCR Master Mix (Agilent Technologies, USA). Total extracted RNA was quantified in spectrophotometer Nano-Drop model DN-1000 and afterwards, its integrity was tested in an agarose gel electrophoresis (0.8% p/v) dyed with ethidium bromide.

Amplification was performed using the following primers:
Aero-F 5'-GAGCGAGAAGGTGACCACCAAGAACC (SEQ ID NO:1), and
Aero-R 5'-TTCCAGTCCCACCACTTCACTTCAC (SEQ ID NO:2) for aerolisin;
Lip-F 5'-GACCCCCTACCTGAACCTGAGCTAC (SEQ ID NO:3), and
Lip-R 5'-AGTGACCCAGGAAGTGCACCTTGAG (SEQ ID NO:4) for Lipase; and
Ser-F 5'-ACGGAGTGCGTTCTTCCTACTCCAG (SEQ ID NO:5), and
Ser-R 5'-CCGTTCATCACACCGTTGTAGTCG (SEQ ID NO:6) for serine protease.

For relative quantitation, 16S rDNA region was used using 1492-R and 27-F primers. Reaction was performed in a real-time thermocycler from Aligent Technologies Stratagene model Mx3000P and relative quantitation and statistical analysis was performed using MxPro software (Aligent Technologies).

Results indicate that the extract produced by *Cobetia marina* strain MM1IDA2H-1 interfere with QS signals produced by *C. violaceum* (FIG. 2). When this microorganism is exposed to the presence of QS signals and AAFOB-1IDA2H extract, no violet phenotype is formed for this bacterium. Absence of this extract restores the violet phenotype in cultures exposed to QS signals (FIG. 2). For determining if AAFOB-1IDA2H extract acts during development of *C. violaceum*, this microorganism was exposed to different concentrations of the extract. In this case, it was not possible to appreciate formation of violet phenotype at different concentrations evaluated (FIG. 3). Thus, it is possible to establish that AAFOB-1IDA2H extract possesses the biological capacity to interfere in the QS system existing in *Chromobacterium violaceum*.

For determining if the interference with QS system affects pathogenic behavior of microorganisms, the effect of the extract was evaluated on the virulence expression of *Aeromonas salmonicida* (FIG. 4), and in the inhibition in formation of biofilms in *Listonella anguillarum* (Table 6).

TABLE 6

Inhibitory activity in biofilm formation of *Listonella anguillarum*.

| Biosurfactant extract concentration (mg/mL) | Inhibition (%) |
| --- | --- |
| 2.5 | 18.0 +/− 16.1 |
| 25 | 39.6 +/− 4.8 |

TABLE 6-continued

Inhibitory activity in biofilm
formation of *Listonella anguillarum*.

| Biosurfactant extract concentration (mg/mL) | Inhibition (%) |
|---|---|
| 50 | 74.8 +/− 5.0 |
| 75 | 86.5 +/− 0.5 |

Results show that AAFOB-1IDA2H extract interferes with QS signals produced by pathogen *Aeromonas salmonicida*. This bacterium produced, during growth, QS signals that can be detected by *Chromobacterium violaceum* CV026, turning its violet phenotype on. Exposition of a supernatant with QS signals in presence of AAFOB-1IDA2H extract avoids formation of violet phenotype in *Chromobacterium violaceum* CV026 (FIG. 4). Therefore, it is possible to establish that AAFOB-1IDA2H extract interferes with QS signals produced by *Aeromonas salmonicida*.

For determining if AAFOB-1IDA2H extract interferes with QS system of *Aeromonas salmonicida*, and affects display of associated virulence factors, quantitation assays of transcripts from *Aeromonas salmonicida* exposed to products of *Cobetia marina* strain MM1IDA2H-1 were made (FIG. 5). Results indicate that genes associated with virulence of Aerolisin (FIG. 5A) and serine protease (FIG. 5B), are significantly suppressed when *Aeromonas salmonicida* is grown in presence of products generated by *Cobetia marina* strain MM1IDA2H-1.

On the other hand, biofilm formation of *Listonella anguillarum* was studied in presence of AAFOB-1IDA2H extract. In this fish pathogenic bacterium, biofilm forming behavior is QS dependent and is considered of importance for development of pathologies caused by this microorganism. Obtained results indicate that the presence of AAFOB-1IDA2H extract, at a concentration of 75 mg/ml, inhibits film formation up to 86.5% (Table 6). Results indicate that AAFOB-1IDA2H extract produced by *Cobetia marina* strain MM1IDA2H-1 interferes with QS system, and can be used to avoid display of virulence mechanism of pathogenic bacteria for fish.

Toxicity Assay and Immunity in Fish.

Additionally, a toxicity and immunity in fish analysis was performed in *Oncorhynchus mykiss* in culture through food incorporating as active agent the product denominated AAFOB-1IDA2H.

The field assay was performed in 12 tanks of 0.18 cubic meters of salt water in which 15 fish of approximately 120 grams each of *O. mykiss* specie, which represents a density of 10 kilograms per cubic meter for each tank. Tanks were separated in three types of diet, of which two were food in form of pellets elaborated with AAFOB-1IDA2H with doses of 4.17 and 8.34 grams of AAFOB-1IDA2H per kilogram of delivered food. Third diet was a negative control, without AAFOB-1IDA2H.

For maintenance of axenic conditions, doses were treated with ionizing radiation. Fish were fed for at least 30 days for evaluating the following parameters: 1. Survival to the diet based on AAFOB, 2. Antimicrobial activity in blood plasma on pathogen *Aeromonas salmonicida*, 3. Effect of diets in intestinal microflora at metabolic level, 4. Effect on immunological activity at intestinal level. After subjecting the fish to respective diets, tanks were sampled for samples of blood serum and intestines for corresponding analyses.

As results of this assay, it was obtained that the product: 1. Affects the display of virulence factors of fish pathogens by itself, 2. It is able to induce a specific immune response mediated by TNF-alpha in kidneys and IL-1B in gills, 3. Does not show toxicity by being directly incorporated in cultured fish, 4. Presents physical properties that allow to form stable emulsions with oil mixtures and thus, can be added to fish food in the form of pellets during the elaboration production process, 5. The elaborated food containing the active agent AAFOB-1IDA2H when used in a fish diet for *O. mykiss* of 120 grams is not toxic and stimulates their immune system, which is mediated by a higher antimicrobial activity of blood plasma in fish subjected to the diet compared to a control diet without AAFOB-1IDA2H additive.

This represents that the diet formulated in base to AAFOB-1IDA2H presents an effect at the level of microflora and thus, physiological and immunological levels.

Therefore, among the advantages of the present invention, the following can be emphasized:
 i) unlike antibiotics, the extract of the invention does not generate resistance;
 ii) unlike antibiotics, the extract of the invention acts selectively over conducts that determine virulence in pathogenic microorganisms;
 iii) the extract of the invention shows activity in concentrations similar to antibiotics;
 iv) unlike antibiotics, the extract of the invention, and given that it is a natural product, its use is not subjected to the same environmental regulations, sanitary, or others;
 v) just like with antibiotics used in aquaculture, the extract can be added in food during extrusion process;
 vi) unlike antibiotics, other antimicrobials and even other Quorum Sensing inhibitors, no steps of chemical synthesis or hemi-synthesis are required;
 vii) the extract of the invention is not toxic for different cell lines nor fish;
 viii) the extract of the invention comes from a marine bacterium which is not pathogenic for fish.
 ix) the extract of the invention is a mixture of biodegradable compounds and thus, is environmentally safe;
 x) the extract of the invention produced by the strain corresponds to a mixture of fatty acids presenting an activity interfering with QS system;
 xi) features and physical properties of the extract of the invention, such as emulsifier, allow its addition in dry food during or after extrusion process.

Table 7 emphasizes the distinctive features between the use of the biosurfactant extract of the present invention and two broadly used in aquaculture antibiotics.

TABLE 7

Properties of biosurfactant produced by *Cobetia marina* strain MM1IDA2H-1 and some selected antibiotics.

| | Ampicillin | | Tetracyclin | | Biosurfactant extract | |
|---|---|---|---|---|---|---|
| | YES | NO | YES | NO | YES | NO |
| Bactericidal, bacteriostatic, bacteriolytic activity.[1] | ● | ○ | ● | ○ | ○ | ● |
| Inhibition of QS system.[2] | ○ | ● | ○ | ● | ● | ○ |
| Selective inhibition of bacterial virulence.[3] | ○ | ● | ○ | ● | ● | ○ |

TABLE 7-continued

Properties of biosurfactant produced by *Cobetia marina* strain MM1IDA2H-1 and some selected antibiotics.

| | Ampicillin | | Tetracyclin | | Biosurfactant extract | |
|---|---|---|---|---|---|---|
| | YES | NO | YES | NO | YES | NO |
| Generation of resistance | ● | ○ | ● | ○ | ○ | ● |
| Natural origin | ○ | ● | ○ | ● | ● | ○ |
| Synthetic origin | ● | ○ | ● | ○ | ○ | ● |

[1] Measured on *Chromobacterium violaceum*
[2] Measured on *Chromobacterium violaceum* and *Chromobacterium violaceum* CV026.
[3] Measured on pathogenic bacterium *Aeromonas salmonicida*.

Table 8 shows the main advantages of the use of the method of the present invention for obtaining a biosurfactant, based on biosynthesis of an extracellular extract by the strain of the present invention.

TABLE 8

Advantages of the production process of BS extract using *Cobetia* strain MM1IDA2H-1.

| | SI | NO |
|---|---|---|
| Reduction in water consumption. | ● | ○ |
| Inducible and controllable process. | ● | ○ |
| Independent of chemical synthesis. | ● | ○ |
| Selective production | ● | ○ |
| Contamination problems | ○ | ○ |

The invention claimed is:

1. A method for preparing a biosurfactant, the method comprising:
   (a) growing *Cobetia marina* strain (MM1IDA2H-1), deposited under registry CECT N° 7764, in a liquid culture medium within a bioreactor for 24 to 48 hours at a temperature between 10 and 35° C., pH 6 to 8; with constant stirring between 100 to 400 rpm and oxygen saturation between 10 to 21% to obtain a culture comprising bacterial cells, extracellular products and inorganic salts;
   (b) separating the bacterial cells from the culture to obtain a liquid supernatant that is free of the bacterial cells and that comprises extracellular products and inorganic salts;
   (c) lyophilizing the liquid supernatant at −80° C. and 10 militorr (1.33 Pa) to obtain a powder comprising the extracellular products and inorganic salts;
   (d) mechanically sieving said powder, with horizontal stirring, to obtain a sieved powder; and
   (e) drying the sieved powder at a temperature between 30 and 50° C. for 20 to 30 hours to obtain the biosurfactant as a dry powder having light yellow color and fatty acids having emulsifier and bioactive properties.

2. The method of claim 1, wherein the liquid culture medium comprises at least: 0.2 g/L magnesium sulfate; 0.02 g/L calcium chloride; 1 g/L monopotassium phosphate; 1 g/L diammonium hydrogen phosphate; 1 g/L potassium nitrite, 0.05 g/L ferric chloride, 0.25 L distilled water, and between 0.75 to 1.5% w/v of an aromatic heterocyclic hydrocarbon containing sulphur as the only carbon source.

3. The method of claim 1, wherein the liquid culture medium is the same medium containing at least 75% in volume of sea water as solubilizing agent.

4. The method of claim 1, wherein the step of separating comprises centrifugation and filtration, wherein the centrifugation is performed between 2,000 to 4,000 rpm for 15 to 20 minutes, and wherein the filtration is performed using a filter cut-off of between 0.22 to 0.45 μm.

5. The method of claim 1, wherein the liquid culture medium comprises dibenzothiophene (DBT) as the only carbon source.

6. The method of claim 5, characterized in that wherein the DBT is in a concentration between 0.75 to 1.5% w/v.

7. A method for treating or avoiding infectious pathologies in an aquaculture in need thereof, the method comprising applying an effective amount of a biosurfactant to the aquaculture, wherein the biosurfactant is prepared by the method of claim 1.

8. The method of claim 7, wherein the infectious pathologies are dependent on a Quorum Sensing system.

9. The method of claim 7, wherein the infectious pathologies are caused by bacteria from genus *Aeromonas, Listonella* and pathogenic fungi in which the virulence is dependent on Quorum Sensing system.

10. The method of claim 9, wherein the infectious pathologies are caused by *Aeromonas salmonicida* or *Listonella anguillarum*.

\* \* \* \* \*

SEQUENCE LISTING

<160> NUMBER OF SEQ ID NOS: 6

<210> SEQ ID NO 1
<211> LENGTH: 26
<212> TYPE: DNA
<213> ORGANISM: Artificial Sequence
<220> FEATURE:
<223> OTHER INFORMATION: Synthesized

<400> SEQUENCE: 1
gagcgagaag gtgaccacca agaacc                                       26

<210> SEQ ID NO 2
<211> LENGTH: 25
<212> TYPE: DNA
<213> ORGANISM: Artificial Sequence
<220> FEATURE:
<223> OTHER INFORMATION: Synthesized

<400> SEQUENCE: 2
ttccagtccc accacttcac ttcac                                        25

<210> SEQ ID NO 3
<211> LENGTH: 25
<212> TYPE: DNA
<213> ORGANISM: Artificial Sequence
<220> FEATURE:
<223> OTHER INFORMATION: Synthesized

<400> SEQUENCE: 3
gaccccctac ctgaacctga gctac                                        25

<210> SEQ ID NO 4
<211> LENGTH: 25
<212> TYPE: DNA
<213> ORGANISM: Artificial Sequence
<220> FEATURE:
<223> OTHER INFORMATION: Synthesized

<400> SEQUENCE: 4
agtgacccag gaagtgcacc ttgag                                        25

<210> SEQ ID NO 5
<211> LENGTH: 25
<212> TYPE: DNA
<213> ORGANISM: Artificial Sequence
<220> FEATURE:

```
<223> OTHER INFORMATION: Synthesized

<400> SEQUENCE: 5
acggagtgcg ttcttcctac tccag                                              25

<210> SEQ ID NO 6
<211> LENGTH: 24
<212> TYPE: DNA
<213> ORGANISM: Artificial Sequence
<220> FEATURE:
<223> OTHER INFORMATION: Synthesized

<400> SEQUENCE: 6
ccgttcatca caccgttgta gtcg                                               24
```